United States Patent
Syed (10) Patent No.: US 9,770,315 B2
(45) Date of Patent: Sep. 26, 2017

(54) WATER FLOSS PICK

(71) Applicant: Seemie N. Syed, Atlanta, GA (US)

(72) Inventor: Seemie N. Syed, Atlanta, GA (US)

(*) Notice: Subject to any disclaimer, the term of this patent is extended or adjusted under 35 U.S.C. 154(b) by 31 days.

(21) Appl. No.: 15/139,261

(22) Filed: Apr. 26, 2016

(65) Prior Publication Data

US 2016/0235508 A1  Aug. 18, 2016

Related U.S. Application Data (62) Division of application No. 12/512,643, filed on Jul. 30, 2009, now Pat. No. 9,375,299.

(51) Int. Cl.
| | |
|---|---|
| *A61C 1/10* | (2006.01) |
| *A61C 15/04* | (2006.01) |
| *A61C 17/02* | (2006.01) |
| *A61L 2/025* | (2006.01) |
| *A61L 2/10* | (2006.01) |
| *A61L 2/16* | (2006.01) |

(52) U.S. Cl.
CPC ........ *A61C 15/046* (2013.01); *A61C 17/0202* (2013.01); *A61C 17/0214* (2013.01); *A61L 2/025* (2013.01); *A61L 2/10* (2013.01); *A61L 2/16* (2013.01)

(58) Field of Classification Search
CPC .............. A61C 15/046; A61C 17/0202; A61C 17/0214; A61L 2/025; A61L 2/10; A61L 2/16
USPC .... 433/82, 80, 125; 132/322, 323, 327, 309, 132/326; 128/80, 125, 62, 66; 123/232, 123/309, 322, 326, 327
See application file for complete search history.

(56) References Cited

U.S. PATENT DOCUMENTS

| | | | |
|---|---|---|---|
| 2,208,031 A * | 7/1940 | Hooper | A61C 17/0214 251/303 |
| 3,472,247 A | 10/1969 | Borsum et al. | |
| 3,902,510 A | 9/1975 | Roth | |
| 4,031,908 A | 6/1977 | Ting | |
| 4,319,595 A * | 3/1982 | Ulrich | A46B 11/063 132/309 |
| 4,845,859 A | 7/1989 | Evans | |
| 4,883,080 A | 11/1989 | Lang | |
| 4,888,487 A | 12/1989 | Ritter | |
| 4,903,688 A | 2/1990 | Bibby et al. | |
| 5,023,460 A | 6/1991 | Foster, Jr. et al. | |
| 5,094,256 A | 3/1992 | Barth | |
| 5,160,194 A | 11/1992 | Feldman | |

(Continued)

*Primary Examiner* — Cris L Rodriguez
*Assistant Examiner* — Mirayda A Aponte
(74) *Attorney, Agent, or Firm* — Rahman LLC (57) ABSTRACT

A multi-piece apparatus for performing dental hygiene includes a head portion including a concave support member; a floss attachment; and a tapered hollow water access portion. The hollow water access portion includes a water intake component continuous with a water exit component. A mechanism is connected to the head portion that reduces bacteria from the head portion. A handle portion is connected to the head portion and includes a first handle end; a second handle end; and a fluid aqueduct extending an entire internal length of the handle portion, wherein the fluid aqueduct is aligned with the water intake component and extends within the head portion. A hose is connected to the handle portion, wherein the hose is positioned to direct water to traverse through the fluid aqueduct.

19 Claims, 5 Drawing Sheets

(56) References Cited

U.S. PATENT DOCUMENTS

| | | | |
|---|---|---|---|
| 5,170,809 A | | 12/1992 | Imai et al. |
| 5,230,624 A | * | 7/1993 | Wolf .................... A61C 1/0076 433/82 |
| 5,246,367 A | | 9/1993 | Ito et al. |
| 5,570,709 A | | 11/1996 | Haddad et al. |
| 5,906,213 A | * | 5/1999 | Diffendal ................ A46B 7/04 132/309 |
| 5,967,155 A | | 10/1999 | Marcon |
| 6,099,813 A | | 8/2000 | Gipson, II |
| 6,171,559 B1 | | 1/2001 | Sanders et al. |
| 6,315,220 B1 | * | 11/2001 | Grubb .................... E03C 1/086 239/588 |
| 6,390,103 B1 | | 5/2002 | Manso |
| 6,602,071 B1 | | 8/2003 | Ellion et al. |
| 6,953,940 B2 | | 10/2005 | Leighley et al. |
| 7,080,980 B2 | * | 7/2006 | Klupt .................... A61C 17/222 15/167.1 |
| 7,147,468 B2 | | 12/2006 | Snyder et al. |
| 7,270,129 B1 | | 9/2007 | Rehkemper |
| 7,325,554 B2 | | 2/2008 | Ochs |
| 7,370,658 B2 | | 5/2008 | Chodorow et al. |
| 7,467,946 B2 | | 12/2008 | Rizoiu et al. |
| 7,621,687 B1 | | 11/2009 | Rehkemper et al. |
| 2002/0074012 A1 | * | 6/2002 | Marcon ................ A61C 15/041 132/321 |
| 2005/0000537 A1 | | 1/2005 | Junkins |
| 2005/0079096 A1 | | 4/2005 | Brown-Skrobot et al. |
| 2006/0174911 A1 | | 8/2006 | Naruse |
| 2006/0275349 A1 | | 12/2006 | Andrews et al. |
| 2008/0041412 A1 | | 2/2008 | Jansheski et al. |
| 2009/0056044 A1 | | 3/2009 | Rizoiu et al. |

* cited by examiner

Providing an apparatus having a disposable head portion including a concave support member, a hollow water access portion having a water intake component structurally continuous with a water exit component, and a floss attachment. — 101

↓

Simultaneously directing pressurized water onto the floss attachment and manually positioning the floss attachment between teeth of a user. — 102

WATER FLOSS PICK

CROSS-REFERENCE TO RELATED APPLICATIONS

This application is a divisional of U.S. patent application Ser. No. 12/512,643, filed on Jul. 30, 2009, entitled "Water Floss Pick," the complete disclosure of which, in its entirety, is herein incorporated by reference.

BACKGROUND

Technical Field

The embodiments herein generally relate to dental devices, and, more particularly, to dental devices used for maximizing bacterial and particle removal from teeth.

Description of the Related Art

Tooth decay has been implicated in the cause and progression of many systemic and organ related diseases. Dental professionals recommend the removal of dental plaque from the surface of teeth on at least a daily basis. Plaque is a clear sticky substance which continually forms in the mouth above and below the "gumlines". Plaque can calcify and form a hardened material, tartar; however, cleaning around each tooth prevents calcification of plaque. This cleaning aids in the prevention of cavities and related dental problems. It is well recognized that brushing with a toothbrush is not sufficient to avoid these problems.

Present flossing devices are ineffective to obtain maximum bacterial removal and therefore, prevent the formation of plaque. Floss used repeatedly simply spreads bacteria. Water devices do not remove the amount of material needed to avoid tooth decay, while present vibration devices do not address the need for floss and water flow as required elements in dental cleaning.

What is needed is an apparatus that continuously removes debris generated by highly effective flossing methods which is hygienic and is designed to recognize and have the potential to incorporate additional substances for maximum efficiency in oral cleaning.

SUMMARY

In view of the foregoing, an embodiment herein provides an apparatus for performing dental hygiene comprising a disposable head portion comprising a concave support member; a hollow water access portion comprising a water intake component structurally continuous with a water exit component; and a floss attachment connected to the concave support member and the water exit component, wherein the floss attachment is positioned substantially parallel to the water intake component continuous with the water exit component. The apparatus further comprises a handle portion operatively connected to the head portion and comprising a motor; and a fluid aqueduct adjacent to the motor, wherein the aqueduct is aligned with the water intake component, and wherein the motor is positioned to direct water through the aqueduct. The apparatus further comprises a base operatively connected to the handle portion and comprising a reservoir; and a hose connecting the reservoir to the handle portion.

Preferably, the handle portion comprises a first end comprising at least one aperture; and an opposed second end positioned adjacent to the motor. Moreover, the water intake component may comprise at least one flexible detent aligned for insertion into the at least on aperture of the first end of the handle portion, wherein upon insertion the water intake component is aligned with the aqueduct. Furthermore, the water exit component preferably defines a centralized aperture, wherein the centralized aperture is positioned to direct pressurized water traversing the water exit component onto the floss attachment. The water exit component may comprise a first contact component that supports the floss attachment. Additionally, the concave support member may comprise a second contact component that supports the floss attachment. Also, the base may comprise a re-charging contact member.

Moreover, the second end of the handle portion may comprise a charge contact complementary to the re-charging contact member on the base. The apparatus may further comprise a power cord that is integral with the re-charging contact member of the base. Additionally, the apparatus may further comprise a mechanism operatively connected to the handle portion that reduces bacteria from the handle portion. Furthermore, the handle portion may comprise a switch that controls the flow of water through the aqueduct and provides vibration control of the floss attachment. Also, the reservoir may comprise a regulating switch that controls water flow into the hose. Preferably, the hollow water access portion of the disposable head portion is tapered.

Another embodiment provides an apparatus for performing dental hygiene comprising a disposable head portion comprising a concave support member, a hollow water access portion having a water intake component continuous with a water exit component, and a floss attachment, wherein the floss attachment is substantially longitudinally aligned to a longitudinal axis of the water intake component a longitudinal axis of the water exit component; a handle operatively connected to the disposable head portion comprising an aqueduct, wherein the aqueduct is aligned with the water intake component, the water exit component, and the floss attachment; and a hose connection removably attached to the handle, wherein the hose is positioned to direct pressurized water to traverse the aqueduct.

Preferably, the handle comprises a first handle end comprising at least one aperture; and a second handle end positioned opposite to the first handle end. Moreover, the water intake component may comprise at least one flexible detent aligned for insertion into the at least on aperture of the first handle end, wherein upon insertion the water intake component is aligned with the aqueduct. Also, the water exit component preferably defines a centralized aperture, wherein the centralized aperture is positioned to direct pressurized water traversing the water exit component onto the floss attachment. Furthermore, the hose preferably comprises a first hose end and a second hose end, wherein the first hose end comprises a first hose attachment device, and wherein the handle comprises a handle attachment device on the second handle end which is complimentary to the first hose attachment device on the first hose end of the hose. Additionally, the first hose attachment device may comprise a flexible lip integral with a disc component, wherein the disc component defines a centralized aperture positioned to align with the aqueduct of the handle when attached.

Moreover, the hose may comprise a second hose attachment device on the second hose end, wherein the second hose attachment device comprises an expandable U-shaped component. Also, a separate reservoir may be continuous to the hose via a release valve. Furthermore, the hose may have a screen. Additionally, the hose may be integral with a separate chamber having a spring-loaded button to force objects into the hose and onto the screen.

Another embodiment provides a system for performing dental hygiene comprising a motorized cleaning device comprising a water intake component and an oppositely positioned water exit component; a power component operatively connected to the motorized cleaning device; a floss component attached to the water exit component; a reservoir component operatively connected to the motorized cleaning device; and an aqueduct component attached to the reservoir component, wherein the aqueduct component traverses the motorized cleaning device, wherein the aqueduct component is positioned to direct pressurized water onto the floss component, and wherein the aqueduct component comprises a first end attached to the reservoir component; and a second end that contacts the water intake component of the motorized cleaning device.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which.

DETAILED DESCRIPTION OF PREFERRED EMBODIMENTS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein provide a water floss apparatus and method for dental hygiene. The embodiments herein prevent tooth decay and gum disease by providing a tool that combines a pressurized flow of water onto a tooth flossing component in order to synergistically remove the maximum amount of impacted food, particles, and bacteria. The end result is effective cleaning that can be performed at home or in a dentist office. Referring now to the drawings, and more particularly to FIGS. 1A through 5, where similar reference characters denote corresponding features consistently throughout the figures, there is shown a preferred embodiment.

Figure 1A:
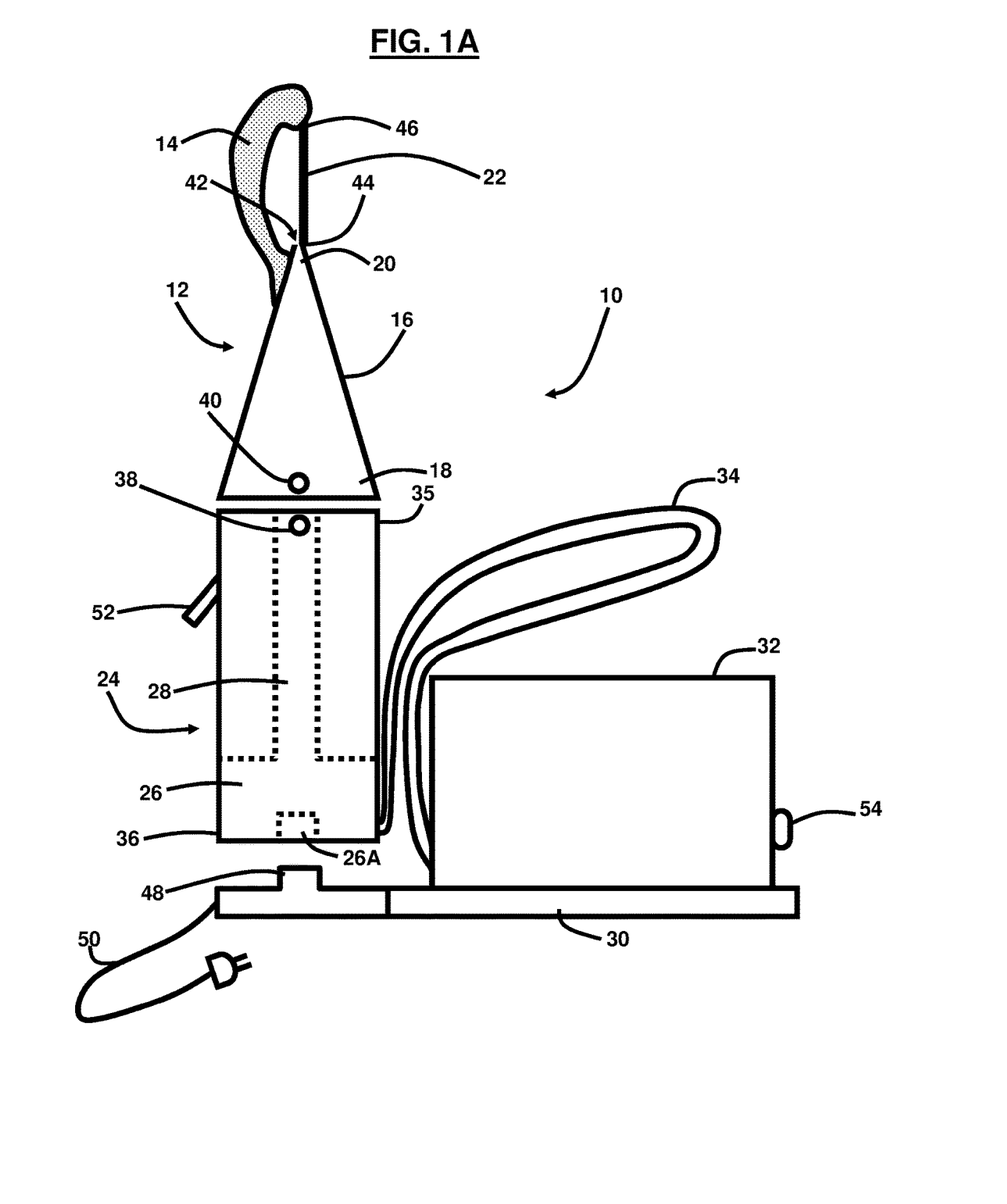
FIG. 1A is a side view of a water floss pick according to an embodiment herein.
Figure 1B:
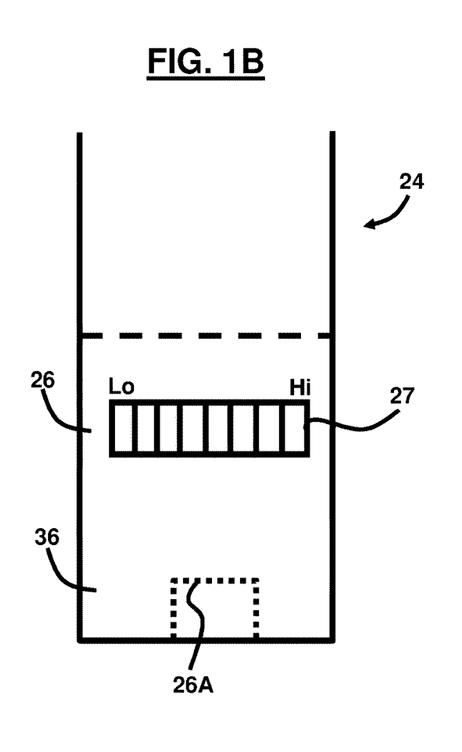
FIG. 1B illustrates an alternate configuration of the embodiment of FIG. 1A according to an embodiment herein.
Figure 2:
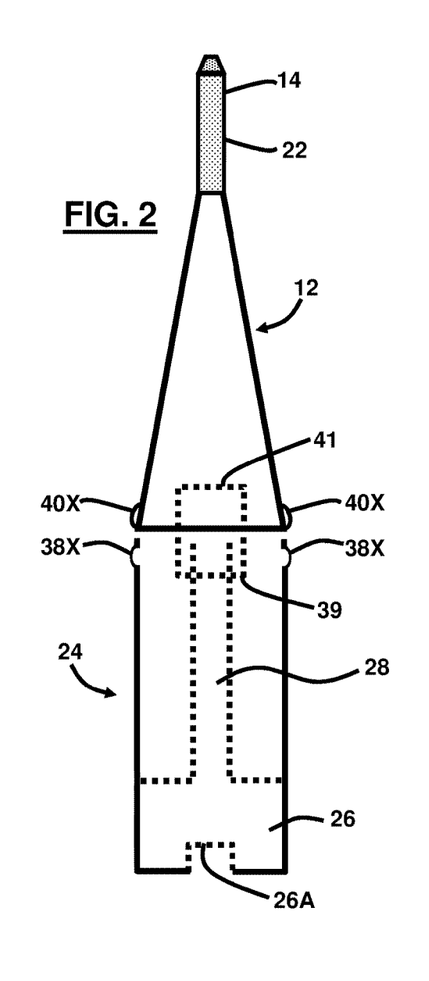
FIG. 2 is a front view of a handle and head portion of the water floss pick of FIG. 1A according to an embodiment herein.

Referring to FIGS. 1A through 2, an apparatus 10 for performing dental hygiene includes a disposable head portion 12 having a concave support member 14, a hollow water access portion 16 having a water intake component 18 structurally continuous with a water exit component 20, and a floss attachment 22. The floss attachment 22 is substantially parallel to the water intake component 18 continuous with the water exit component 20. The hollow water access portion 16 is tapered, narrowing from the water intake component 18 to the water exit component 20 to focus a "stream" of pressurized water as described herein. The handle portion 24 includes a water pressure motor 26 and an aqueduct 28 (both illustrated in phantom), wherein the aqueduct 28 is aligned with the water intake component 18 of the disposable head portion 12. In one embodiment, the aqueduct 28 extends within the disposable head portion 12. In another embodiment, no aqueduct is included as the tapered structure of the hollow water access portion 16 facilitates a high-pressure discharge. A base 30 includes a reservoir 32 which houses water and/or mouthwash and/or any other type of dental cleaning fluid, wherein a water hose 34 connects the reservoir 32 to the handle 24. The water pressure motor 26 is positioned to direct pressurized water from the reservoir 32 to traverse through the aqueduct 28.

The handle portion 24 has a first end 35 and a second end 36, wherein the first end 35 has at least one aperture 38. The water intake component 18 includes at least one flexible detent 40 aligned for insertion into the at least on aperture 38 of the first end 35 of the handle portion 24. As can best be seen in FIG. 2, multiple apertures 38X and detents 40X can be aligned to ensure a secure fit. The detachable connection of the disposable head 12 and the handle 24 can include a variety of configurations; e.g. snaps, slide, and hook, etc., to provide a secure attachment, and such configurations are mechanically advantageous over screw-on mechanisms in that they provide for quick attach/detach, and screw-on mechanisms typically result in damaged threads (especially if configured with plastic material or low-grade metal material), which result in the inability to properly secure the two complementary sides, or if the threads are metal, then they are prone to rust and corrosion since the handle portion 24 and disposable head 12 will become wet during use. Use of higher grade metal for constructing the threads would increase the manufacturing costs and device cost and would add to the overall weight of the device, which are all undesirable. Therefore, using a screw-on mechanism is not preferred in accordance with the embodiments herein, and configuring the embodiments herein to have a screw-on mechanism would result in increased cost, increased complexity, reduced device lifetime, and accordingly would not be advantageous.

Upon insertion of the handle 24 to the disposable head 12, the water intake component 18 is aligned with the aqueduct 28 so as to allow pressurized water (not shown) from the reservoir 32 to flow into the disposable head 12 and onto the floss attachment 22 during use. As shown in FIG. 2, the disposable head 12 and handle 24 each comprise respective complementary secondary alignment and locking features 41, 39 that provide further alignment of the disposable head 12 with the handle 24 and to provide enhanced locking of the disposable head 12 with the handle 24 upon the flow of water through the handle 24 and head 12. In this regard, the secondary alignment and locking features 41, 39 improve the overall stability of the head 12 with respect to the handle 24 to prevent inadvertent dislodging of the head 12 during use or over time. The secondary alignment and locking features 41, 39 may work independently or in tandem with the multiple apertures 38X and detents 40X to provide a secure alignment and locking of the head 12 with respect to the handle. The secondary alignment and locking features 41, 39 may be embodied in any appropriate configuration including, but not limited to, locking tabs, snap-on mechanisms, buttons, male/female lock, pins, etc. In one embodiment, the water pressure motor 26 pressurizes the water as it enters the handle portion 24. In another embodiment, the water from the reservoir 32 becomes pressurized once it traverses through the aqueduct 28 and then through the tapered hollow water access portion 16 that creates a pressurized flow of water through the narrow water exit component 20 such that the speed of the water exiting water exit component 20 is greater than the speed of the water entering and traversing through the aqueduct 28 and the water intake component 18. The water exit component 20 defines a centralized aperture 42, wherein the centralized aperture 42 is positioned to direct pressurized water traversing the water exit component 20 onto the floss attachment 22. As shown in FIG. 1A, the centralized aperture 42 may direct the water traversing the water exit component 20 onto the floss attachment 22 in a direction along the floss attachment 22 from a first contact component 44 for the floss attachment 22 to a second contact component 46 for the floss attachment 22. That is, water may be directed parallel to the floss attachment 22 rather than perpendicular to the floss component 22 by the centralized aperture 42.

The water exit component 20 includes a first contact component 44 for the floss attachment 22 and the support component 14 comprises a second contact component 46 for the floss attachment 22. In one embodiment, a floss storage mechanism (not shown) is included to house extra floss. In another embodiment, there is no particular floss storage mechanism included. Rather, after use, the entire head portion 12 is simply discarded. This is feasible since the head portion 12 is inexpensive. Also, the floss may be constructed using a wide assortment of materials; some having enhanced material property characteristics which permits re-use of the floss thereby negating the necessity of having to discard the head portion 12 (with floss) after each single use.

The base 30 comprises a re-charging contact member 48 and the second end of the handle 36 includes a charge contact 26A (shown in phantom) integral with the motor 26 complementary to the re-charging contact member 48 on the base 30, wherein the re-charging contact member 48 of the base 30 is integral with a power cord 50. The handle 24 includes an on/off switch 52 which controls the flow of water through the aqueduct 28 and the reservoir 32 includes a regulating switch 54 which controls water flow into the hose 34. The water pressure motor 26 may also provide enhanced vibration to the floss attachment 22 to increase the cleaning action afforded by the floss attachment 22. In this embodiment, the on/off switch 52 may further include a vibration setting, which enhances the overall vibration of the device when on. Referring to FIG. 1B, a Hi/Lo rolling mechanism 27 is illustrated in isolation to show an optional vibration setting for the motor 26 as described above. This will give user preference regarding vibration if one handle 24 is being used with multiple disposable heads 12.

Preferably, the disposable head 12, handle 24, reservoir 32, and base 30 are made of a hard plastic which can be cleaned with water, and which are lightweight and not susceptible to rust. The motor 26 is made of a combination of metal and plastic components as would be recognized by those skilled in the art for a motor commercially available for similar use. The motor 26 is positioned within the handle 24 so as to be sealed from excess water during use. The motor 26 is in a separate compartment (not shown) within the handle 24 that separates the motor 26 from any liquid that may escape from the aqueduct 28. Most commonly, the motor 26 is sealed by a plastic membrane. The re-charging contact member 48 and charge contact 26A are made of a conductive substance to transfer charge. One of skill in the art would appreciate that although the current embodiment is a re-chargeable design, a battery powered design would also be possible while staying with the basic concept of the embodiments herein.

Figure 3A:
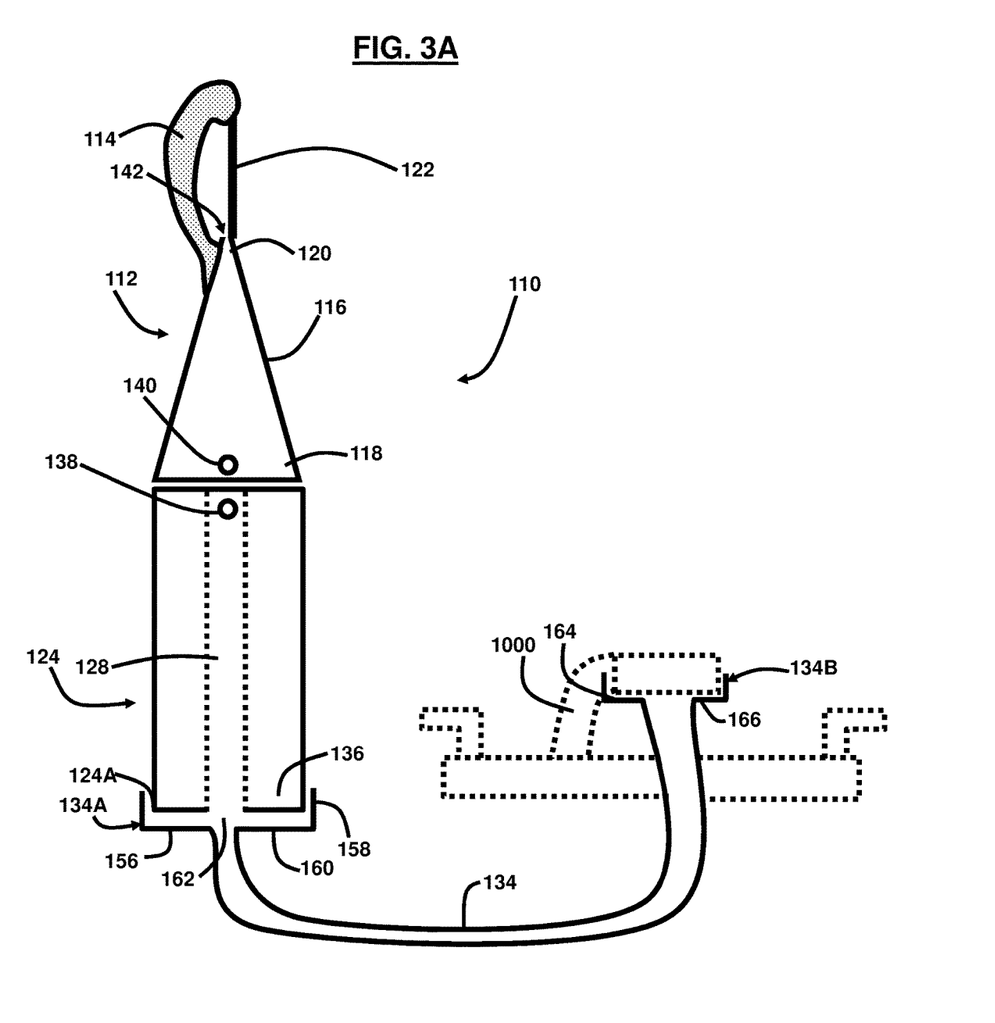
FIG. 3A is a front view of another embodiment of the water floss pick illustrating a water source according to an embodiment herein.

FIG. 3A illustrates an apparatus 110 for performing dental hygiene that is directly attached to a water source; e.g., a faucet 1000, according to another embodiment herein. The apparatus 110 includes a disposable head portion 112 having a concave support member 114, a hollow water access portion 116 having a water intake component 118 structurally continuous with a water exit component 120, and a floss attachment 122. As in the embodiment shown in FIGS. 1A through 2, the floss attachment 122 is substantially parallel to the water intake component 118 continuous with the water exit component 120. A handle portion 124 includes an aqueduct 128 (shown in phantom) aligned with the water intake component 118. The hollow water access portion is attached to the handle 124 via corresponding indent/detent features 138, 140.

A water hose connection 134 is removably attached to the handle 124, and is positioned to direct pressurized water to traverse the aqueduct 128. Water is obtained from a faucet 1000 (shown in phantom); accordingly no motor is required for this embodiment. Moreover, the water becomes pressurized by traversing the tapered hollow water access portion 116 due to the smaller exit area of the central aperture 142 compared with the entry area of the water intake component 118. The water exit component 120 defines the central aperture 142 positioned to direct pressurized water traversing the water exit component 120 onto the floss attachment 122. The water hose 134 has a first end 134A and a second end 134B, wherein the first end 134A includes an attachment device 156. The handle 124 has an attachment device 124A on a second end 136 which is complimentary to the attachment device 156 on the first end 134A of the water hose 134. The attachment device 156 on the first end 134A of the water hose 134 includes a flexible lip 158 integral with a disc component 160. The disc component 160 defines a centralized aperture 162 positioned to align with the aqueduct 128 of the handle 124 when attached.

The water hose 134 includes a second attachment device 164 on the second end 134B which has an expandable U-shaped component 166. The U-shaped component 166 is directly attached to the faucet 1000 which supplies water which traverses the water hose 134, aqueduct 128, hollow water access portion 116, and onto the floss component 122 during use. The hose 134 and corresponding attachment devices 156, 164 may be made from plastic, rubber, or any suitable flexible, lightweight, and corrosive-free material. The attachment devices 156, 164 facilitate a tight/secure attachment to the corresponding ends of the hose 134 to prevent any leakage of the water and/or mouthwash.

Figure 3B:
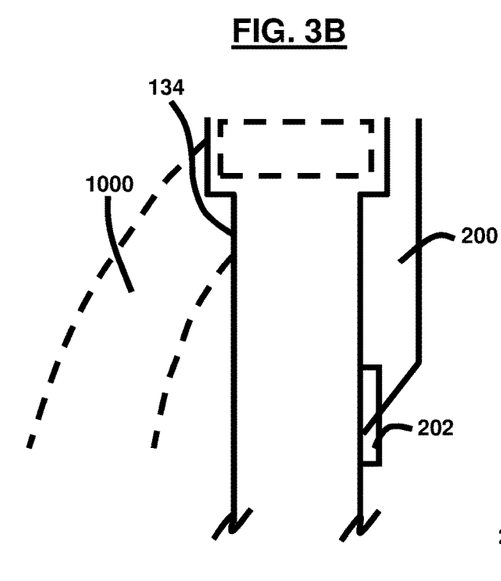
FIG. 3B illustrates an alternate configuration of the embodiment of FIG. 3A according to an embodiment herein.
Figure 3C:
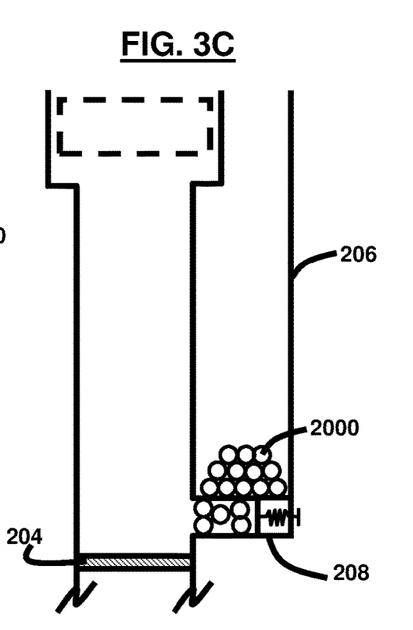
FIG. 3C illustrates another alternate configuration of the embodiment of FIG. 3A according to an embodiment herein.

Referring to FIGS. 3B and 3C, alternate configurations of the embodiments herein are illustrated wherein the hose 134 is directly connected to the faucet 1000, and wherein a separate compartment 200 to hold mouthwash, or other desired substance, is combined with the water coming from the faucet 1000.

Referring to FIG. 3B, a separate reservoir 200 is continuous to the hose 134 via a release valve 202; the hose 134 coming directly from the faucet 1000 for mixing with the mouthwash to be added. The release valve 202 is illustrated as simple sliding partition but those skilled in the art would recognize multiple configurations are possible while remaining within the spirit herein.

Referring to FIG. 3C, in yet another configuration, rather than having liquid mouthwash being added, the hose 134 could include a screen or filter 204 to hold "pellets" 2000 that when combined with water creates a mouthwash-like fluid. In this configuration, the pellets 2000 are housed in a separate chamber 206 attached to the hose 134 and discharged into the water stream by pressing a spring-loaded button 208 to force a defined amount of pellets 2000 into the hose 134 and water stream. As the spring-loaded button 208 is released another defined load of pellets 2000 is supplied from the separate chamber 206.

Figure 4:
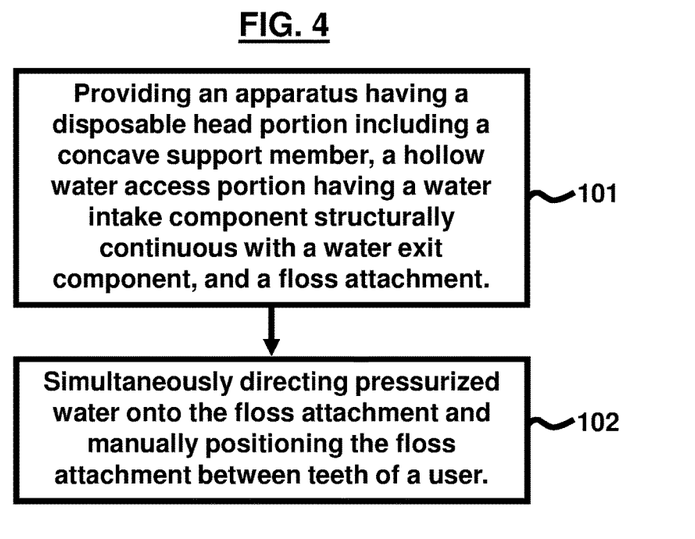
FIG. 4 is a flow diagram illustrating a preferred method according to an embodiment herein.

FIG. 4, with reference to FIGS. 1A through 3C, illustrates a flow diagram according to another embodiment herein, wherein a method is provided for performing dental hygiene floss removal which includes the steps of providing (101) an apparatus 10, 110 having a disposable head portion 12, 112 including a concave support member 14, 114, a hollow water access portion 16, 116 having a water intake component 18, 118 structurally continuous with a water exit component 20, 120, and a floss attachment 22, 122, wherein the floss attachment 22, 122 is substantially parallel to the water intake component 18, 118 continuous with the water exit component 20, 120. The apparatus 10, 110 further includes a handle portion 24, 124 including a water pressure motor 26 (in apparatus 10 and no motor in apparatus 110) and an aqueduct 28, 128, wherein the aqueduct 28, 128 is aligned with the water intake component 18, 118. Preferably, the longitudinal axis of the floss attachment 22, 122 is aligned with the longitudinal axes of each of the water intake component 18, 118, the water exit component 20, 120, and the handle portion 24, 124. In addition the apparatus 10 includes a base 30 supporting a reservoir 32, wherein a water hose 34 connects the reservoir to the handle 24. The water pressure motor 26 is positioned to direct pressurized water to traverse the aqueduct 28. The method also includes the step of simultaneously directing (102) pressurized water onto the floss attachment 22, 122 and manually positioning the floss attachment 22, 122 between teeth (not shown) of a user (not shown). Additionally, the embodiments herein may be used to clean teeth, dentures, partials, braces, and any other types of dental implants and inserts.

Figure 5:
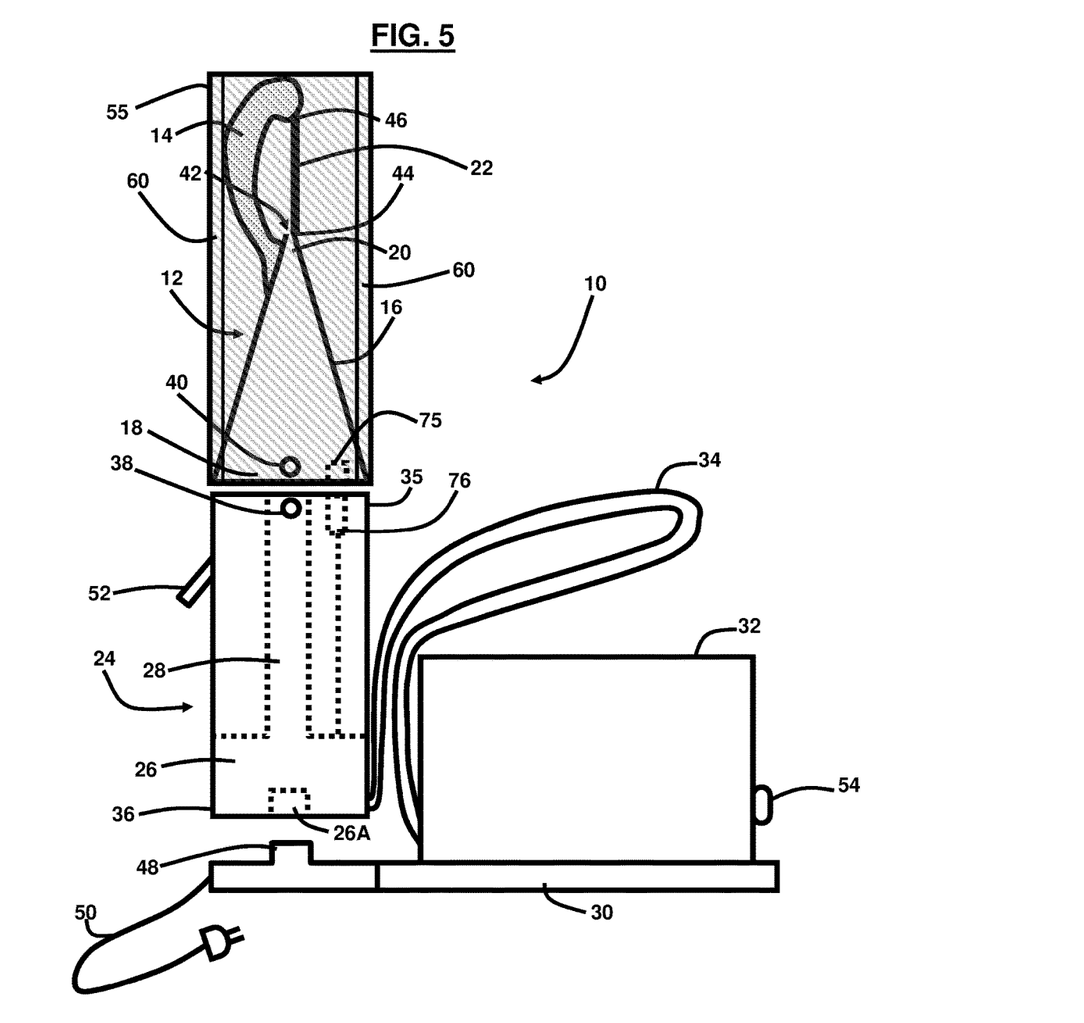
FIG. 5 is a front view of another embodiment of the water floss pick illustrating a sterile-providing component according to an embodiment herein.

FIG. 5, with reference to FIGS. 1A through 4, illustrates a front view of another embodiment herein including a sterile-providing component 55, which may be embodied as a cap-like device, which comprises a mechanism 60 to enhance the cleanliness of the head 12. The mechanism 60 may include an ultraviolet (UV) light source mechanism, ultrasonic/vibration mechanism, chemical agent, or any other bacteria-removing mechanism that further removes bacteria and germs from the head 12. The sterile-providing component 55 may by powered by the charge contact 26A integral with the motor 26 and complementary to the recharging contact member 48 charging contact member 48 and power cord 50 operatively connected to the handle 24. In such an embodiment, complementary electrical contact members 75, 76 may be provided to facilitate the on/off (electrical power) of the sterile-providing component 55. These contact members 75, 76 may be shielded from water that is inside the head 12 and handle 24 by a sealing mechanism (not shown) that shields the water inside the head 12 and handle 24 from other internal components. Additionally, the on/off switch 52 may be configured to provide the on/off feature of the sterile-providing component 55. Accordingly, when the sterile-providing component 55 is powered on, the mechanism 60 removes bacteria from the head 12. Alternatively, the sterile-providing component 55 may be powered by an independent power source (e.g., a battery or power cord), which may provide power to the sterile-providing component 55 or to the entire apparatus 10, 110.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A multi-piece apparatus for performing dental hygiene comprising:
   a head portion comprising:
   a concave support member comprising a first end and a second end;
   a floss attachment comprising a first end and a second end, wherein said first end of said floss attachment is connected to said first end of said concave support member; and
   a tapered hollow water access portion comprising a first end and a second end, wherein the first end of said tapered hollow water access portion is operatively connected to the second end of said concave support member, wherein said hollow water access portion comprises a water intake component continuous with a water exit component, wherein said water intake component is positioned at said second end of said hollow water access portion, wherein said water exit component is positioned at said first end of said hollow water access portion, wherein said second end of said hollow water access portion is diametrically larger than said first end of said hollow water access portion, wherein said water exit component comprises a first contact component that supports said floss attachment at said second end of said floss attachment, and wherein said concave support member comprises a second contact component at said first end of said concave support member that supports said floss attachment at said first end of said floss attachment, wherein said water exit component defines a central aperture positioned to direct water traversing said water exit component onto said floss attachment in a direction from said first end of said floss attachment to said second end of said floss attachment substantially parallel to said floss attachment;

a cap like device operatively connected to said head portion comprising a mechanism operatively connected to said head portion that reduces bacteria from said head portion, wherein said mechanism comprises any of an ultraviolet (UV) light source mechanism, an ultrasonic/vibration mechanism, and a chemical agent;

a handle portion detachably connected to said head portion, said handle portion comprising:
- a first handle end comprising at least one aperture;
- a second handle end positioned opposite to said first handle end, wherein said second handle end comprises a handle attachment device; and
- a fluid aqueduct extending an entire internal length of said handle portion, wherein said fluid aqueduct is longitudinally aligned with said water intake component and extends within said head portion, wherein said water intake component of said head portion comprises at least one flexible detent configured for insertion into said at least one aperture of said first handle end, and wherein upon insertion, said water intake component is longitudinally aligned with said fluid aqueduct;

a hose detachably connected to said handle portion, wherein said hose comprises:
- a first end comprising a first hose attachment device that is complimentary to said handle attachment device, wherein said hose attachment device comprises a flexible lip integral with a disc component, and wherein said disc component defines a centralized aperture positioned to align with said fluid aqueduct of said handle portion;
- a second end comprising a second hose attachment device comprising an expandable U-shaped component, wherein said U-shaped component is configured to directly attach to a water source; and
- a filter positioned inside said hose and in between said first end and said second end, wherein said hose is positioned to direct water to traverse through said fluid aqueduct.

2. The apparatus of claim 1, further comprising a compartment connected to said hose.

3. The apparatus of claim 2, wherein said compartment is configured to hold any of mouthwash and pellets.

4. The apparatus of claim 3, wherein said compartment comprises a valve connected to said hose.

5. The apparatus of claim 4, wherein said valve releases said mouthwash from said compartment into said hose to combine with water coming from said water source.

6. The apparatus of claim 3, wherein said valve comprises a sliding partition.

7. The apparatus of claim 3, wherein said hose comprises an opening connecting said hose to said compartment.

8. The apparatus of claim 7, further comprising a spring-loaded button adjacent to said compartment to force a defined amount of said pellets through said opening and into said hose.

9. The apparatus of claim 8, wherein said filter retains said pellets that have been forced into said hose by said spring-loaded button.

10. The apparatus of claim 9, wherein said pellets are combined with water coming from said water source in said hose creating a mouthwash-like fluid.

11. The apparatus of claim 10, wherein said mouthwash-like fluid passes through said filter.

12. The apparatus of claim 2, wherein said compartment is configured to hold any of a fluid and a solid.

13. The apparatus of claim 1, wherein said floss attachment is substantially parallel to said water intake component.

14. The apparatus of claim 1, wherein said tapered hollow water access portion is configured to cause a speed of said water exiting said water exit component to be greater than a speed of said water entering and traversing through said fluid aqueduct and said water intake component.

15. The apparatus of claim 1, wherein said hose, said first hose attachment device, and said second hose attachment device comprises any of plastic and rubber.

16. The apparatus of claim 1, wherein said hose, said first hose attachment device, and said second hose attachment device are flexible.

17. The apparatus of claim 1, wherein said hose, said first hose attachment device, and said second hose attachment device comprise corrosive-free material.

18. The apparatus of claim 1, wherein said water source comprises a faucet.

19. The apparatus of claim 1, wherein said compartment is continuous with said hose.

* * * * *